US008404816B2

(12) United States Patent
Couto et al.

(10) Patent No.: US 8,404,816 B2
(45) Date of Patent: Mar. 26, 2013

(54) METHODS FOR ANTIBODY ENGINEERING

(75) Inventors: Fernando Jose Rebelo Do Couto, Pleasanton, CA (US); Kristin B. Hendricks, San Carlos, CA (US); S. Ellen Wallace, Sunnyvale, CA (US); Guo-Liang Yu, Hillsborough, CA (US)

(73) Assignee: Epitomics, Inc., Burlingame, CA (US)

( * ) Notice: Subject to any disclaimer, the term of this patent is extended or adjusted under 35 U.S.C. 154(b) by 0 days.

(21) Appl. No.: 13/100,089

(22) Filed: May 3, 2011

(65) Prior Publication Data

US 2012/0003671 A1 Jan. 5, 2012

Related U.S. Application Data

(63) Continuation of application No. 12/263,002, filed on Oct. 31, 2008, now Pat. No. 7,960,517, which is a continuation of application No. 10/984,473, filed on Nov. 8, 2004, now Pat. No. 7,462,697.

(51) Int. Cl.
*C12P 21/08* (2006.01)
*A61K 39/00* (2006.01)
*G01N 33/53* (2006.01)

(52) U.S. Cl. ............... 530/387.3; 530/387.1; 424/133.1; 435/7.1

(58) Field of Classification Search ........................ None
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 5,225,539 A | 7/1993 | Winter | |
| 5,530,101 A | 6/1996 | Queen | |
| 5,585,089 A | 12/1996 | Queen | |
| 5,639,641 A | 6/1997 | Pedersen | |
| 5,693,761 A | 12/1997 | Queen | |
| 5,693,762 A | 12/1997 | Queen | |
| 6,180,370 B1 | 1/2001 | Queen | |
| 6,329,551 B1 | 12/2001 | Nakagome | |
| 6,331,415 B1 | 12/2001 | Cabilly | |
| 6,342,587 B1 | 1/2002 | Barbas | |
| 2003/0198638 A1 | 10/2003 | Watkins | |
| 2004/0086979 A1 | 5/2004 | Zhang et al. | |
| 2005/0033031 A1 | 2/2005 | Couto | |

FOREIGN PATENT DOCUMENTS

WO 2004/016740 A2 2/2004

OTHER PUBLICATIONS

JP Application No. 2007-540061, first Notice of Reasons for Rejection (with translation), issued Jun. 22, 2011, 11pgs.
Becker et al., Somatic Diversification of Immunoglobulin Heavy Chain VDJ Genes: Evidence for Somatic Gene Conversion in Rabbits, Cell, 1990, 63:987-97.
Bendig, "Humanization of rodent monoclonal antibodies by CDR grafting", Methods: A Companion to Methods in Enzymology, 1995, 8:83-93.
De Pascalis et al., Grafting of "Abbreviated" Complementarity-Determining Regions Containing Specificity-Determining Residues Essential for Ligand Contact to Engineer a Less Immunogenic Humanized Monoclonal Antibody, J Imm, 2002, 169:3076-84.
Delagrave et al., Effects of Humanization by Variable Domain Resurfacing on the Antiviral Activity of a Single-Chain Antibody Against Respiratory Syncytial Virus, Prot. Eng., 1999, 12: 357-62.
Green, Antibody Engineering Via Genetic Engineering of the Mouse: Xenomouse Strains Are a Vehicle for the Facile Generation of Theraputic Human Monoclonal Antibodies, J Imm Methods, 1999, 231:11-23.
Knight et al., Molecular Basis of the Allelic Inheritance of Rabbit Immunoglobulin VH Allotypes: Implications for the Generation of Antibody Diversity, Cell, 1990, 60: 963-70.
Mehr et al., Analysis of Mutational Lineage Trees From Sites of Primary and Secondary Ig Gene Diversification in Rabbits and Chickens, J Immunol., 2004, 172:4790-6.
Morea et al., Antibody Modeling: Implications for Engineering and Design, Methods, 2000, 20:267-79.
Popkov et al., Rabbit Immune Repertoires as Sources for Therapeutic Monoclonal Antibodies: The Impact of Kappa Allotype-Correlated Variation in Cysteine Content on Antibody Libraries Selected by Phage Display, J Mol Biol, 2003, 325:325-35.
Rader et al,.The Rabbit Antibody Repertoire as a Novel Source for the Generation of Therapeutic Human Antibodies, J. Biol. Chem., 2000, 275:13668-76.
Rader et al., A Phage Display Approach for Rapid Antibody Humanization: Designed Combinatorial V Gene Libraries, Proc. Natl. Acad. Sci., 1998, 95:8910-15.
Roguska et al., A Comparison of Two Murine Monoclonal Antibodies Humanized by CDR-Grafting and Variable Domain Resurfacing, Prot. Eng., 1996, 9:895-904.
Roguska et al., Humanization of Murine Monoclonal Antibodies Through Variable Domain Resurfacing, Proc. Natl. Acad. Sci., 1994, 91:969-73.
Steinberger et al., Generation and Characterization of a Recombinant Human CCR5-Specific Antibody, J. Bio. Chem., 2000, 275:36073-78.
Vaswani et al., Humanized Antibodies as Potential Therapeutic Drugs, Ann. Allergy Asthma Immunol., 1998, 81:105-19.
JP Application No. 2011-279530, first Notice of Reasons for Rejection (with transl.), issued Feb. 2012, 9pgs.

*Primary Examiner* — Anne Gussow
(74) *Attorney, Agent, or Firm* — James S. Keddie; Bozicevic, Field & Francis, LLP

(57) ABSTRACT

The invention provides a method for identifying positions of an antibody that can be modified without significantly reducing the binding activity of the antibody. In many embodiments, the method involves identifying a substitutable position in a parent antibody by comparing its amino acid sequence to the amino acid sequences of a number of related antibodies that each bind to the same antigen as the parent antibody. The amino acid at the substitutable position may be substituted for a different amino acid without significantly affecting the activity of the antibody. The subject methods may be employed to change the amino acid sequence of a CDR without significantly reducing the affinity of the antibody of the antibody, in humanization methods, or in other antibody engineering methods. The invention finds use in a variety of therapeutic, diagnostic and research applications.

11 Claims, 10 Drawing Sheets

```
              ----CDR1--   FW1    -CDR2--   FW3    ----CDR3---
Position      abcdefghij          klmnopq          rstuvwxyzα
ANTIBODY
   1          RTAATMCLFQ  - FW2 - RFWTVTA - FW3 -  PSASHTVQIT
   2          RTAATMCLFQ  - FW2 - RFWTVSA - FW3 -  PSASHTVNIT
   3          RTGATMCLFQ  - FW2 - RFWTVTA - FW3 -  PSHSHTVQIT
   4          RTAATVCLFQ  - FW2 - RFWTVSA - FW3 -  PSASHTVQIT
   5          RTCATMCLFQ  - FW2 - RFWTVTA - FW3 -  PSASHTVQIT
   6          RTAATMCLFQ  - FW2 - RYWTVTA - FW3 -  PSQSHTVQIT
   7          RTEATMCLFQ  - FW2 - RFWTVTA - FW3 -  PSASHTVQIT
   8          RTAATICLFQ  - FW2 - RFWTVTA - FW3 -  PSASHTVQIT
   9          RTAATVCLFQ  - FW2 - RWWTVTA - FW3 -  PSASHTVYIT
  10          RTTATMCLFQ  - FW2 - RFWTVTA - FW3 -  PSWSHTVQIT VT positns    ---X---X-------------X---X-------------X----X--
Consensus     RTXATXCLFQ  - FW1 - RXWTVXA - FW2 -  PSXSHTVXIT
```

F

```
Position      abcdefghij - FW2 - klmnopq - FW3 - rstuvwxyzα
ANTIBODY
   1          RTAATMCLFQ - FW2 - RFWTVTA - FW3 - PSASHTVQIT
 human        RTTASGALAQ - FW2 - RFWACFA - FW3 - PAAHQTVYTT
VT positns    ---X--X-------------X---X---------------X----X-- hmAb        RTTATGCLFQ - FW2 - RFWTVFA - FW3 - PSASHTVYIT
```

```
Position      abcdefghij - FW2 - klmnopq - FW3 - rstuvwxyzα
ANTIBODY
   1          RTAATMCLFQ - FW2 - RFWTVTA - FW3 - PSASHTVQIT
 human        RTTASGALAQ - FW2 - RFWACFA - FW3 - PAAHQTVYTT
VT positns    ---X--X-------------X---X---------------X----X-- hmAb        RTTATMCLFQ - FW2 - RFWTVTA - FW3 - PSASHTVYIT
```

T is found at this position in antibody 10

Y is found at this position in antibody 9

```
CARDINSYGYAY         ATDIW
CARSGYAGSS           YYNLW
CARSDYSYGG           AYDIW
CARRVDSTG            TDIW
CGSGYYINI            W
CARGGAGISGYT         YENIW
CARGCPGYG            DNDIW
CARGYWSLD            IW
CVRDSTGISA           LFNVW
CARRGATASHR          WFIIW
CGSGANIENFF          FNAIW
CAREDRSHDYD          YFKIW
CARSQDSGSHDDF        PFNIW
CARSPGGIGD           AFDFW
CARGWVGLN            IW
CARRADGYGY           AYDIW
CARYGASVT            YFNIW
CARFRILVIVLV         PLDLW
CARGATMTMVRG         WLDLW
CARLGLVVV            INIW
```

Fig. 5

```
VK
Strands...-A-      --A'--    ---B----            ---CDR1---              --C--    --C'--    --CDR2--
          -234567890123456789012345 67890abcdef1234567890123456789012345 67890abcdef12345 67
CDR......ccccc.c..............................cccccccccccccccccc..........c...cccccccc..
INT..............................b.b..............................i.i...ii.i............
BUR.........b.b.........23456789012345 67890abcdef12345 67890123456789012345 67890abcdef12345 67

TNFa52:DIVMTQTPASASEPVGGTV-ITCQASQNIY                  NTLAWYQQKPGQPPKLMSLASTLESG
VK1L20:DIQMTQSPSSLSASVGDRV-ITCRASQGIS                  NYLAWYQQKPGKVPKLLIYAASTLQSG
HZD....DIVMTQTPSSASESVGDRV-INCQASQNIY                  NTLAWYQQKPGKPPKLMSLASTLESG

MUTATED RESIDUES
Mutated Rabbit A to Human S at position VK9
Mutated Rabbit P to Human S at position VK14
Mutated Rabbit G to Human D at position VK17
Mutated Rabbit T to Human R at position VK18
Mutated Rabbit Q to Human K at position VK42
Mutated Rabbit K to Human S at position VK63
Mutated Rabbit D to Human S at position VK77
Mutated Rabbit E to Human Q at position VK79
Mutated Rabbit C to Human P at position VK80
Mutated Rabbit A to Human E at position VK81
Mutated Rabbit E to Human K at position VK103
Mutated Rabbit V to Human E at position VK105

RETAINED RESIDUES
CDR contact: Rabbit - V human - Q At position VK3
CDR contact: Rabbit - T human - S At position VK7
Buried res : Rabbit - A human - L At position VK11
Buried res : Rabbit - E human - A At position VK13
CDR contact: Rabbit - N human - T At position VK22
Interf.res.: Rabbit - P human - V At position VK43
CDR contact: Rabbit - M human - H At position VK48
CDR contact: Rabbit - S human - Y At position VK49
CDR contact: Rabbit - E human - D At position VK70
Buried res : Rabbit - A human - V At position VK83
Buried res : Rabbit - V human - I At position VK106

STATS
Number of Rabbit residues = 112
Number of mutations       = 12  11%
Retained Rab residues     = 11  10%
```

FIG. 6

```
      ----D----  ----E----    ----F----  ----CDR3-----
    6         7         8         9         10
    89012345678901234567890123456789012345abcde67890123 4567
    c.c.c...cc.ccc.......b..b..bob.b.....cccccccccccc
    .....b....b...b....b.b.b...bob.b......i.i.........i..b.b.
    890123456789012345678901234567890123456789012345abcde67890123 4567
    VPSRFKGSGSGTEFTLTISDLECADAATYYCQSNHGSNSDSYGNTFGGGTEVVVK
    VPSRFSGSGSGTDFTLTISSLQPEDVATYYCQ                    LTFGGGIKVEIK
    VPSRFSGSGSGTEFTLTISSLQPEDAATYYCQSNHGSNSDSYGNTFGGGIKVEVK
```

FIG. 6 (Cont.)

```
          1         2    ==CDR1===========          4
VK     1234567890123456789 0abcdef1234567890123456789
Set_1 |----------------X--|=================|--X-----|
Set_2 |-------------------|----------------X|X-------|
Set_3 |-------X-----------|---------------X-|XX------|
         1         2    ==CDR1===========         4
VH     1234567890123456789 01ab234567890123456789012a
Set_1 |----------------X--|----X-------------|-X-----|
Set_2 |-------------------|--X-X-------------|-------|
Set_3 |XXXXX------X-------|X---XX-----X--X---|----X--|
```

FIG. 7

SEQUENCE LISTING

```
<160> NUMBER OF SEQ ID NOS: 48

<210> SEQ ID NO 1
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 1

Arg Thr Ala Ala Thr Met Cys Leu Phe Gln Arg Phe Trp Thr Val Thr
1               5                   10                  15

Ala Pro Ser Ala Ser His Thr Val Gln Ile Thr
            20                  25

<210> SEQ ID NO 2
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 2

Arg Thr Ala Ala Thr Met Cys Leu Phe Gln Arg Phe Trp Thr Val Ser
1               5                   10                  15

Ala Pro Ser Ala Ser His Thr Val Asn Ile Thr
            20                  25

<210> SEQ ID NO 3
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 3

Arg Thr Gly Ala Thr Met Cys Leu Phe Gln Arg Phe Trp Thr Val Thr
1               5                   10                  15

Ala Pro Ser His Ser His Thr Val Gln Ile Thr
            20                  25

<210> SEQ ID NO 4
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 4

Arg Thr Ala Ala Thr Val Cys Leu Phe Gln Arg Phe Trp Thr Val Ser
```

Ala Pro Ser Ala Ser His Thr Val Gln Ile Thr
            20                  25

<210> SEQ ID NO 5
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 5

Arg Thr Cys Ala Thr Met Cys Leu Phe Gln Arg Phe Trp Thr Val Thr
1               5                   10                  15

Ala Pro Ser Ala Ser His Thr Val Gln Ile Thr
            20                  25

<210> SEQ ID NO 6
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 6

Arg Thr Ala Ala Thr Met Cys Leu Phe Gln Arg Tyr Trp Thr Val Thr
1               5                   10                  15

Ala Pro Ser Gln Ser His Thr Val Gln Ile Thr
            20                  25

<210> SEQ ID NO 7
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 7

Arg Thr Glu Ala Thr Met Cys Leu Phe Gln Arg Phe Trp Thr Val Thr
1               5                   10                  15

Ala Pro Ser Ala Ser His Thr Val Gln Ile Thr
            20                  25

<210> SEQ ID NO 8
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 8

Arg Thr Ala Ala Thr Ile Cys Leu Phe Gln Arg Phe Trp Thr Val Thr
1               5                   10                  15

Ala Pro Ser Ala Ser His Thr Val Gln Ile Thr
            20                  25

<210> SEQ ID NO 9
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 9

Arg Thr Ala Ala Thr Val Cys Leu Phe Gln Arg Trp Trp Thr Val Thr

Ala Pro Ser Ala Ser His Thr Val Tyr Ile Thr
            20                  25

<210> SEQ ID NO 10
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 10

Arg Thr Thr Ala Thr Met Cys Leu Phe Gln Arg Phe Trp Thr Val Thr
 1               5                  10                  15

Ala Pro Ser Trp Ser His Thr Val Gln Ile Thr
            20                  25

<210> SEQ ID NO 11
<211> LENGTH: 27
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: 3, 6, 12, 16, 20, 25
<223> OTHER INFORMATION: Xaa = Any Amino Acid

<400> SEQUENCE: 11

Arg Thr Xaa Ala Thr Xaa Cys Leu Phe Gln Arg Xaa Trp Thr Val Xaa
 1               5                  10                  15

Ala Pro Ser Xaa Ser His Thr Val Xaa Ile Thr
            20                  25

<210> SEQ ID NO 12
<211> LENGTH: 27
<212> TYPE: PRT
<213> ORGANISM: rabbit

<400> SEQUENCE: 12

Arg Thr Ala Ala Thr Met Cys Leu Phe Gln Arg Phe Trp Thr Val Thr
 1               5                  10                  15

Ala Pro Ser Ala Ser His Thr Val Gln Ile Thr
            20                  25

<210> SEQ ID NO 13
<211> LENGTH: 27
<212> TYPE: PRT
<213> ORGANISM: H. sapiens

<400> SEQUENCE: 13

Arg Thr Thr Ala Ser Gly Ala Leu Ala Gln Arg Phe Trp Ala Cys Phe
 1               5                  10                  15

Ala Pro Ala Ala His Gln Thr Val Tyr Thr Thr
            20                  25

<210> SEQ ID NO 14
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 14

Arg Thr Thr Ala Thr Gly Cys Leu Phe Gln Arg Phe Trp Thr Val Phe

```
                   1               5                  10                 15
Ala Pro Ser Ala Ser His Thr Val Tyr Ile Thr
            20                  25

<210> SEQ ID NO 15
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 15

Arg Thr Thr Ala Thr Met Cys Leu Phe Gln Arg Phe Trp Thr Val Thr
 1               5                  10                  15

Ala Pro Ser Ala Ser His Thr Val Tyr Ile Thr
            20                  25

<210> SEQ ID NO 16
<211> LENGTH: 115
<212> TYPE: PRT
<213> ORGANISM: rabbit

<400> SEQUENCE: 16

Gln Glu Gln Leu Lys Glu Ser Gly Gly Gly Leu Val Thr Pro Gly Gly
 1               5                  10                  15

Thr Leu Thr Leu Thr Cys Thr Ala Ser Gly Phe Thr Ile Ser Ser Tyr
            20                  25                  30

Val Met Thr Trp Val Arg Gln Ala Pro Gly Lys Gly Leu Glu Gly Ile
        35                  40                  45

Gly Tyr Ile Lys Ser Gly Asn Ile Trp Tyr Ala Ser Trp Ala Lys Gly
    50                  55                  60

Arg Phe Thr Ile Ser Arg Thr Ser Thr Thr Val Asp Leu Lys Ile Ile
65                  70                  75                  80

Ser Pro Thr Ile Glu Asp Thr Ala Thr Tyr Phe Cys Ala Arg Gly Gly
                85                  90                  95

Val Tyr Asn Ile Gly Leu Asn Ile Trp Gly Pro Gly Thr Leu Val Thr
            100                 105                 110

Val Ser Ser
        115

<210> SEQ ID NO 17
<211> LENGTH: 115
<212> TYPE: PRT
<213> ORGANISM: rabbit

<400> SEQUENCE: 17

Cys Gln Ser Val Glu Glu Ser Gly Gly Arg Leu Val Thr Pro Gly Gly
 1               5                  10                  15

Ser Leu Thr Leu Thr Cys Thr Val Ser Gly Phe Ser Leu Ser Ser Phe
            20                  25                  30

Val Met Ser Trp Val Arg Gln Ala Pro Gly Lys Gly Leu Glu Ala Ile
        35                  40                  45

Gly Tyr Ile Lys Ser Gly Asn Ile Trp Tyr Ala Asn Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Gly Gly
                85                  90                  95

Leu Tyr Asn Ser Gly Leu Asn Ile Trp Gly Pro Gly Thr Leu Val Thr
```

```
Val Ser Ser
        115

<210> SEQ ID NO 18
<211> LENGTH: 115
<212> TYPE: PRT
<213> ORGANISM: rabbit

<400> SEQUENCE: 18

Cys Gln Ser Val Glu Glu Ser Gly Gly Arg Leu Val Thr Pro Gly Gly
1               5                   10                  15

Ser Leu Thr Leu Thr Cys Thr Val Ser Gly Phe Ser Leu Ser Ser Phe
            20                  25                  30

Val Met Ser Trp Val Arg Gln Ala Pro Gly Lys Gly Leu Glu Ala Ile
        35                  40                  45

Gly Tyr Ile Lys Ser Gly Asn Ile Trp Tyr Ala Ser Trp Ala Lys Gly
    50                  55                  60

Arg Phe Thr Ile Ser Arg Thr Ser Thr Val Asp Leu Lys Met Thr
65                  70                  75                  80

Ser Leu Thr Thr Glu Asp Thr Ala Thr Tyr Phe Cys Ala Arg Gly Gly
                85                  90                  95

Val Tyr Asn Ser Gly Leu Asn Ile Trp Gly Pro Gly Thr Leu Val Thr
            100                 105                 110

Val Ser Ser
        115

<210> SEQ ID NO 19
<211> LENGTH: 119
<212> TYPE: PRT
<213> ORGANISM: rabbit

<400> SEQUENCE: 19

Gln Ser Val Lys Glu Ser Glu Gly Gly Leu Phe Lys Pro Thr Asp Thr
1               5                   10                  15

Leu Thr Leu Thr Cys Thr Val Ser Gly Ile Ser Leu Ser Ser Asn Glu
            20                  25                  30

Ile Ser Trp Val Arg Gln Ala Pro Gly Asn Gly Leu Glu Trp Ile Gly
        35                  40                  45

Tyr Val Gly Asn Gly Gly Met Thr His Tyr Ala Ser Trp Ala Lys Ser
    50                  55                  60

Arg Ser Thr Ile Thr Arg Asn Thr Ser Leu Lys Thr Val Thr Leu Lys
65                  70                  75                  80

Met Thr Ser Leu Thr Ala Ala Asp Thr Gly Thr Tyr Phe Cys Ala Ser
                85                  90                  95

Ser Val Ala Tyr Thr Gly Ile Tyr Tyr Phe Asn Ile Trp Gly Pro Gly
            100                 105                 110

Thr Leu Val Thr Val Ser Ser
        115

<210> SEQ ID NO 20
<211> LENGTH: 119
<212> TYPE: PRT
<213> ORGANISM: rabbit

<400> SEQUENCE: 20

Gln Ser Val Lys Glu Ser Glu Gly Gly Leu Phe Lys Pro Thr Asp Thr
1               5                   10                  15
```

```
Leu Thr Leu Thr Cys Thr Val Ser Gly Phe Ser Leu Asn Ser Asn Glu
            20                  25                  30

Ile Ser Trp Val Arg Gln Ala Pro Gly Asn Gly Leu Glu Trp Ile Gly
            35                  40                  45

Tyr Ile Gly Asn Gly Gly Met Thr His Tyr Ala Ser Trp Ala Lys Gly
        50                  55                  60

Arg Ser Thr Ile Thr Arg Asp Thr Asn Leu Asn Thr Val Thr Leu Lys
65                  70                  75                  80

Met Thr Ser Leu Thr Ala Ala Asp Thr Ala Thr Tyr Phe Cys Ala Ser
                85                  90                  95

Ser Val Glu Tyr Thr Asp Leu Tyr Leu Asn Ile Trp Gly Pro Gly
            100                 105                 110

Thr Leu Val Thr Val Ser Ser
            115

<210> SEQ ID NO 21
<211> LENGTH: 112
<212> TYPE: PRT
<213> ORGANISM: rabbit

<400> SEQUENCE: 21

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Asn Thr
            20                  25                  30

Leu Ala Trp Tyr Gln Gln Lys Pro Gly Gln Pro Pro Lys Leu Leu Met
            35                  40                  45

Ser Leu Ala Ser Thr Leu Glu Ser Gly Val Pro Ser Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn His Gly Ser Asn Ser
                85                  90                  95

Asp Ser Tyr Gly Asn Thr Phe Gly Gly Gly Thr Glu Val Val Val Lys
            100                 105                 110

<210> SEQ ID NO 22
<211> LENGTH: 112
<212> TYPE: PRT
<213> ORGANISM: rabbit

<400> SEQUENCE: 22

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Asn Thr
            20                  25                  30

Leu Ala Trp Tyr Gln Gln Lys Pro Gly Gln Pro Pro Lys Leu Leu Ile
            35                  40                  45

Tyr Val Ala Ser Thr Leu Glu Ser Gly Val Pro Ser Arg Phe Lys Gly
        50                  55                  60

Ser Gly Ser Gly Thr Gln Phe Ser Leu Thr Ile Ser Asp Leu Glu Cys
65                  70                  75                  80

Ala Asp Ala Ala Thr Tyr Tyr Cys Gln Ser Asn His Gly Ser Asn Ser
                85                  90                  95

Asn Ser Tyr Gly Asn Thr Phe Gly Gly Gly Thr Glu Val Val Val Lys
            100                 105                 110
```

```
<210> SEQ ID NO 23
<211> LENGTH: 112
<212> TYPE: PRT
<213> ORGANISM: rabbit

<400> SEQUENCE: 23

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Ser Thr
            20                  25                  30

Leu Ala Trp Tyr Gln Gln Lys Pro Gly Gln Pro Pro Lys Leu Leu Ile
        35                  40                  45

Tyr Leu Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asn His Gly Ser Asn Ser
                85                  90                  95

Asn Ser Tyr Gly Asn Thr Phe Gly Gly Gly Thr Glu Val Val Val Lys
            100                 105                 110

<210> SEQ ID NO 24
<211> LENGTH: 110
<212> TYPE: PRT
<213> ORGANISM: rabbit

<400> SEQUENCE: 24

Leu Val Met Thr Gln Thr Pro Ser Ser Thr Ser Glu Pro Val Gly Gly
1               5                   10                  15

Thr Val Thr Ile Asn Cys Gln Ala Ser Asp Asn Ile Tyr Ser Gly Leu
            20                  25                  30

Ala Trp Tyr Gln Gln Lys Pro Gly Gln Pro Pro Lys Leu Leu Ile Tyr
        35                  40                  45

Asp Ala Ser Asn Leu Glu Thr Gly Val Pro Ser Arg Phe Lys Gly Ser
    50                  55                  60

Gly Ser Gly Thr Gln Phe Thr Leu Thr Ile Ser Gly Val Gln Cys Ala
65                  70                  75                  80

Asp Ala Ala Thr Tyr Tyr Cys Leu Gly Val Tyr Ala Tyr Ser Ser Asp
                85                  90                  95

Asp Gly Ala Ala Phe Gly Gly Gly Thr Glu Val Val Val Lys
            100                 105                 110

<210> SEQ ID NO 25
<211> LENGTH: 110
<212> TYPE: PRT
<213> ORGANISM: rabbit

<400> SEQUENCE: 25

Leu Val Met Thr Gln Thr Pro Ser Ser Thr Ser Glu Pro Val Gly Gly
1               5                   10                  15

Thr Val Thr Ile Asn Cys Gln Ala Ser Asp Asn Ile Tyr Arg Gly Leu
            20                  25                  30

Ala Trp Tyr Gln Gln Lys Pro Gly Gln Pro Pro Lys Gln Leu Ile Tyr
        35                  40                  45

Asp Ala Ser Thr Leu Gln Ser Gly Val Pro Ser Arg Phe Lys Gly Ser
    50                  55                  60

Gly Ser Gly Thr Gln Phe Thr Leu Thr Ile Ser Gly Val Gln Cys Asp
65                  70                  75                  80
```

Asp Ala Ala Thr Tyr Tyr Cys Leu Gly Val Tyr Gly Tyr Ser Ser Asp
            85                  90                  95

Asp Gly Ala Ala Phe Gly Gly Gly Thr Glu Val Val Lys
            100                 105                 110

<210> SEQ ID NO 26
<211> LENGTH: 17
<212> TYPE: PRT
<213> ORGANISM: H. sapiens

<400> SEQUENCE: 26

Cys Ala Arg Asp Ile Asn Ser Tyr Gly Tyr Ala Thr Asp Ile
1               5                   10                  15

Trp

<210> SEQ ID NO 27
<211> LENGTH: 15
<212> TYPE: PRT
<213> ORGANISM: H. sapiens

<400> SEQUENCE: 27

Cys Ala Arg Ser Gly Tyr Ala Gly Ser Ser Tyr Tyr Asn Leu Trp
1               5                   10                  15

<210> SEQ ID NO 28
<211> LENGTH: 15
<212> TYPE: PRT
<213> ORGANISM: H. sapiens

<400> SEQUENCE: 28

Cys Ala Arg Ser Asp Tyr Ser Tyr Gly Gly Ala Tyr Asp Ile Trp
1               5                   10                  15

<210> SEQ ID NO 29
<211> LENGTH: 13
<212> TYPE: PRT
<213> ORGANISM: H. sapiens

<400> SEQUENCE: 29

Cys Ala Arg Arg Val Asp Ser Thr Gly Thr Asp Ile Trp
1               5                   10

<210> SEQ ID NO 30
<211> LENGTH: 10
<212> TYPE: PRT
<213> ORGANISM: H. sapiens

<400> SEQUENCE: 30

Cys Gly Ser Gly Tyr Tyr Ile Asn Ile Trp
1               5                   10

<210> SEQ ID NO 31
<211> LENGTH: 17
<212> TYPE: PRT
<213> ORGANISM: H. sapiens

<400> SEQUENCE: 31

Cys Ala Arg Gly Gly Ala Gly Ile Ser Gly Tyr Thr Tyr Phe Asn Ile
1               5                   10                  15

Trp

<210> SEQ ID NO 32
<211> LENGTH: 14
<212> TYPE: PRT

<213> ORGANISM: H. sapiens

<400> SEQUENCE: 32

Cys Ala Gly Cys Pro Gly Tyr Gly Asp Asn Asp Ile Trp
1               5                   10

<210> SEQ ID NO 33
<211> LENGTH: 11
<212> TYPE: PRT
<213> ORGANISM: H. sapiens

<400> SEQUENCE: 33

Cys Ala Arg Gly Tyr Trp Ser Leu Asp Ile Trp
1               5                   10

<210> SEQ ID NO 34
<211> LENGTH: 15
<212> TYPE: PRT
<213> ORGANISM: H. sapiens

<400> SEQUENCE: 34

Cys Val Arg Asp Ser Thr Gly Ile Ser Ala Leu Phe Asn Val Trp
1               5                   10                  15

<210> SEQ ID NO 35
<211> LENGTH: 16
<212> TYPE: PRT
<213> ORGANISM: H. sapiens

<400> SEQUENCE: 35

Cys Ala Arg Arg Gly Ala Thr Ala Ser His Arg Trp Phe Thr Ile Trp
1               5                   10                  15

<210> SEQ ID NO 36
<211> LENGTH: 16
<212> TYPE: PRT
<213> ORGANISM: H. sapiens

<400> SEQUENCE: 36

Cys Gly Ser Gly Ala Asn Ile Glu Asn Glu Phe Phe Asn Ala Ile Trp
1               5                   10                  15

<210> SEQ ID NO 37
<211> LENGTH: 16
<212> TYPE: PRT
<213> ORGANISM: H. sapiens

<400> SEQUENCE: 37

Cys Ala Arg Gly Asp Arg Ser His Asp Tyr Asp Tyr Phe Lys Ile Trp
1               5                   10                  15

<210> SEQ ID NO 38
<211> LENGTH: 18
<212> TYPE: PRT
<213> ORGANISM: H. sapiens

<400> SEQUENCE: 38

Cys Ala Arg Ser Gln Asp Ser Gly Ser His Asp Asp Phe Pro Phe Asn
1               5                   10                  15

Ile Trp

<210> SEQ ID NO 39
<211> LENGTH: 15
<212> TYPE: PRT
<213> ORGANISM: H. sapiens

-continued

```
<400> SEQUENCE: 39

Cys Ala Arg Ser Pro Gly Gly Ile Gly Asp Ala Phe Asp Pro Trp
1               5                   10                  15

<210> SEQ ID NO 40
<211> LENGTH: 11
<212> TYPE: PRT
<213> ORGANISM: H. sapiens

<400> SEQUENCE: 40

Cys Ala Arg Gly Trp Val Gly Leu Asn Ile Trp
1               5                   10

<210> SEQ ID NO 41
<211> LENGTH: 15
<212> TYPE: PRT
<213> ORGANISM: H. sapiens

<400> SEQUENCE: 41

Cys Ala Arg Arg Ala Asp Ser Tyr Gly Tyr Ala Tyr Asp Ile Trp
1               5                   10                  15

<210> SEQ ID NO 42
<211> LENGTH: 14
<212> TYPE: PRT
<213> ORGANISM: H. sapiens

<400> SEQUENCE: 42

Cys Ala Arg Tyr Gly Ala Ser Val Thr Tyr Phe Asn Ile Trp
1               5                   10

<210> SEQ ID NO 43
<211> LENGTH: 17
<212> TYPE: PRT
<213> ORGANISM: H. sapiens

<400> SEQUENCE: 43

Cys Ala Arg Phe Arg Ile Leu Val Ile Val Leu Val Pro Leu Asp Leu
1               5                   10                  15

Trp

<210> SEQ ID NO 44
<211> LENGTH: 17
<212> TYPE: PRT
<213> ORGANISM: H. sapiens

<400> SEQUENCE: 44

Cys Ala Arg Gly Ala Thr Met Thr Met Val Arg Gly Trp Leu Asp Leu
1               5                   10                  15

Trp

<210> SEQ ID NO 45
<211> LENGTH: 13
<212> TYPE: PRT
<213> ORGANISM: H. sapiens

<400> SEQUENCE: 45

Cys Ala Arg Leu Gly Leu Val Val Val Ile Asn Ile Trp
1               5                   10

<210> SEQ ID NO 46
<211> LENGTH: 112
<212> TYPE: PRT
```

```
<213> ORGANISM: rabbit

<400> SEQUENCE: 46

Asp Ile Val Met Thr Gln Thr Pro Ala Ser Ala Ser Glu Pro Val Gly
1               5                   10                  15

Gly Thr Val Thr Ile Asn Cys Gln Ala Ser Gln Asn Ile Tyr Asn Thr
            20                  25                  30

Leu Ala Trp Tyr Gln Gln Lys Pro Gly Gln Pro Pro Lys Leu Leu Met
        35                  40                  45

Ser Leu Ala Ser Thr Leu Glu Ser Gly Val Pro Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Val Tyr Cys Gln Ser Asn His Gly Ser Asn Ser
                85                  90                  95

Asp Ser Tyr Gly Asn Thr Phe Gly Gly Gly Thr Glu Val Val Val Lys
            100                 105                 110

<210> SEQ ID NO 47
<211> LENGTH: 101
<212> TYPE: PRT
<213> ORGANISM: H. sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Val Tyr Cys Gln Leu Thr Phe Gly Gly Gly Thr
                85                  90                  95

Lys Val Glu Ile Lys
            100

<210> SEQ ID NO 48
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 48

Asp Ile Val Met Thr Gln Thr Pro Ser Ser Ala Ser Glu Ser Val Gly
1               5                   10                  15

Asp Arg Val Thr Ile Asn Cys Gln Ala Ser Gln Asn Ile Tyr Asn Thr
            20                  25                  30

Leu Ala Trp Tyr Gln Gln Lys Pro Gly Lys Pro Pro Lys Leu Leu Met
        35                  40                  45

Ser Leu Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80
```

```
-continued

Glu Asp Ala Ala Thr Tyr Tyr Cys Gln Ser Asn His Gly Ser Asn Ser
                85                  90                  95

Asp Ser Tyr Gly Asn Thr Phe Gly Gly Gly Thr Lys Val Glu Val Lys
            100                 105                 110
```

METHODS FOR ANTIBODY ENGINEERING

CROSS-REFERENCING

This application is a continuation of U.S. patent application Ser. No. 12/263,002, filed on Oct. 31, 2008, which application is a continuation of U.S. patent application Ser. No. 10/984,473, filed on Nov. 8, 2004, and issued as U.S. Pat. 7,462,697.

FIELD OF THE INVENTION

The field of this invention is antibodies, particularly methods for engineering; e.g., humanizing, monoclonal antibodies.

BACKGROUND OF THE INVENTION

Because of their ability to target virtually any molecule with exquisite specificity, monoclonal antibodies have the potential to become one of the main therapeutic agents of the future. Though this potential was recognized several years ago, however the first attempts to fulfill the potential were disappointing because monoclonal antibodies used in therapy elicit a strong immune response in patients (Schroff, 1985 Cancer. Res. 45:879-85, Shawler. J Immunol 1985 135:1530-5), even at low doses (Dillman, Cancer Biother. 1994 9:17-28). Scientists predict that human antibodies would not cause such adverse immune responses. However, no suitable methods exist for producing human monoclonal antibodies. Alternative technologies to make human antibodies using, for example, phage display and transgenic animals have been developed more recently but are not widely used for therapeutic purposes.

The immunogenicity of antibodies depends on many factors, including the method of administration, the number of injections, the dosage, the nature of the conjugation, the specific fragment utilized, the state of aggregation and the nature of the antigen (e.g., Kuus-Reichel, Clin. Diagn. Lab. Immunol. 1994 1:365-72), Many or most of these factors can be manipulated in order to decrease an immune response. However, if the original antibody sequence is recognized as "dangerous" or "foreign", the chances are that sooner or later a strong immune response will prevent the use of that antibody in therapy.

In order to decrease these responses, efforts have been made to replace as much as possible of the non-human sequence of an antibody with human sequences using recombinant DNA technology. Towards this end, chimeric antibodies containing human antibody light chain and heavy chain constant domains that are joined to mouse antibody variable light chain and heavy chain domains have been employed. Chimeric antibodies still contain a large number of non-human amino acid sequences in the variable regions and, as such, a significant immune response may be mounted against such antibodies. CDR grafting is another humanization technique in which the antigen binding portions or "complementarity determining regions" (CDRs) of monoclonal antibodies are grafted by recombinant DNA technologies into the DNA sequences encoding the framework (i.e. the non-CDR region) of human antibody heavy and light chains. One technical problem of CDR grafted antibodies is that they usually show considerable decreased affinity. To restore increase the affinity of CDR grafted antibodies, certain original key framework residues (e.g., residues that are thought to be involved in determining the conformation of the CDRs) are reintroduced into the CDR grafted antibody. Using a different humanization approach, Roguska devised a "resurfacing" strategy for mouse antibodies where only exposed residues that are different to exposed residues of a human antibody are substituted.

However, although antibodies humanized by the above methods can show reduced immunogenicity in human patients (Moreland, Arthritis Rheum 1993 36:307-18) many humanized antibodies are still highly immunogenic to a large proportion of patients. This is thought to be because the CDRs themselves are immunogenic (Ritter, Cancer Res 2001 61:6851-9; Welt, Clin Cancer Res 2003 9:1338-46).

A10 of the methods described above require that the CDR regions of the non-human antibody remain unchanged during the humanization process in order to maintain antibody specificity and affinity. However, since non-human CDR regions are themselves immunogenic in humans, methods for humanizing the CDR regions of a non-human antibody without significantly reducing the binding activity of the antibody are highly desirable. The identification of suitable methods for humanizing the CDR regions of a non-human antibody has been a daunting, if not impossible, task for the medical and research community.

Accordingly, there is an ongoing need for improved methods for making non-human antibodies that are less immunogenic in humans and other mammalian hosts. In particular, there is a need for humanization methods that reduce the immunogenicity of CDR regions of a non-human antibody in humans. The present invention meets this, and other, needs.

Literature

References of interest include: U.S. Pat. Nos. 6,331,415 B1, 5,225,539, 6,342,587, 4,816,567, 5,639,641, 6,180,370, 5,693,762, 4,816,397, 5,693,761, 5,530,101, 5,585,089, 6,329,551, and publications Morea et al., *Methods* 20: 267-279 (2000), *Ann. Allergy Asthma Immunol.* 81:105419 (1998), Rader et al., *J. Biol. Chem.* 276:13668-13676 (2000), Steinberger et al., *J. Bio. Chem.* 275: 36073-36078 (2000), Roguska et al., *Proc. Natl. Acad. Sci.* 91: 969-973 (1994), Delagrave et al., *Prot. Eng.* 12: 357-362 (1999), Rogusca et al., *Prot. Eng.* 9: 895-904 (1996), Knight and Becker, Cell 60: 963-970 (1990); Becker and Knight, Cell 63:987-997 (1990) Popkov, J Mol Biol 325:325-35 (2003); Rader et al., Proc. Natl. Acad. Sci. 95:8910-8915; Mehr et al., J. Immunol. 172: 4790-6 (2004) and De Pascalis et al. J. Imm. 2002, 169:3076-3084.

SUMMARY OF THE INVENTION

The invention provides a method for identifying positions of an antibody that can be modified without significantly reducing the binding activity of the antibody. In many embodiments, the method involves identifying a substitutable position in a parent antibody by comparing its amino acid sequence to the amino acid sequences of a number of related antibodies that each bind to the same antigen and epitope as the parent antibody. The amino acid at the substitutable position may be substituted for a different amino acid without significantly affecting the activity of the antibody. The subject methods may be employed to change the amino acid sequence of a CDR without significantly reducing the affinity of the antibody of the antibody, in humanization methods, or in other antibody engineering methods. The invention finds use in a variety of therapeutic, diagnostic and research applications.

These and other advantages and features of the invention will become apparent to those persons skilled in the art upon reading the details of the invention as more fully described below.

BRIEF DESCRIPTION OF THE DRAWINGS

FIG. 2 is an amino acid sequence alignment illustrating an exemplary method by which substitutable positions within a CDR region may be identified. From top to bottom, the amino acid sequences shown in FIG. 2 are SEQ ID NOS: 1-11.

FIG. 3 is two panels showing an exemplary amino acid sequence alignment illustrating one aspect of an exemplary method by which the CDR regions of an antibody may be humanized. From top to bottom, the amino acid sequences shown in FIG. 3 are SEQ ID NO: 12; SEQ ID NO: 13; SEQ ID NO: 14; SEQ ID NO: 12; SEQ ID NO: 13; SEQ ID NO: 15.

FIG. 5 shows the amino acid sequence of 20 exemplary VH3 regions of a rabbit antibodies. From top to bottom, the amino acid sequences shown in FIG. 5 are SEQ ID NOS: 26-45.

FIG. 6 is an exemplary amino acid sequence alignment illustrating one aspect of an exemplary method by which a rabbit antibody may be humanized. From top to bottom, the amino acid sequences shown in FIG. 6 are SEQ ID NOS: 46-48.

DEFINITIONS

Figure 1:
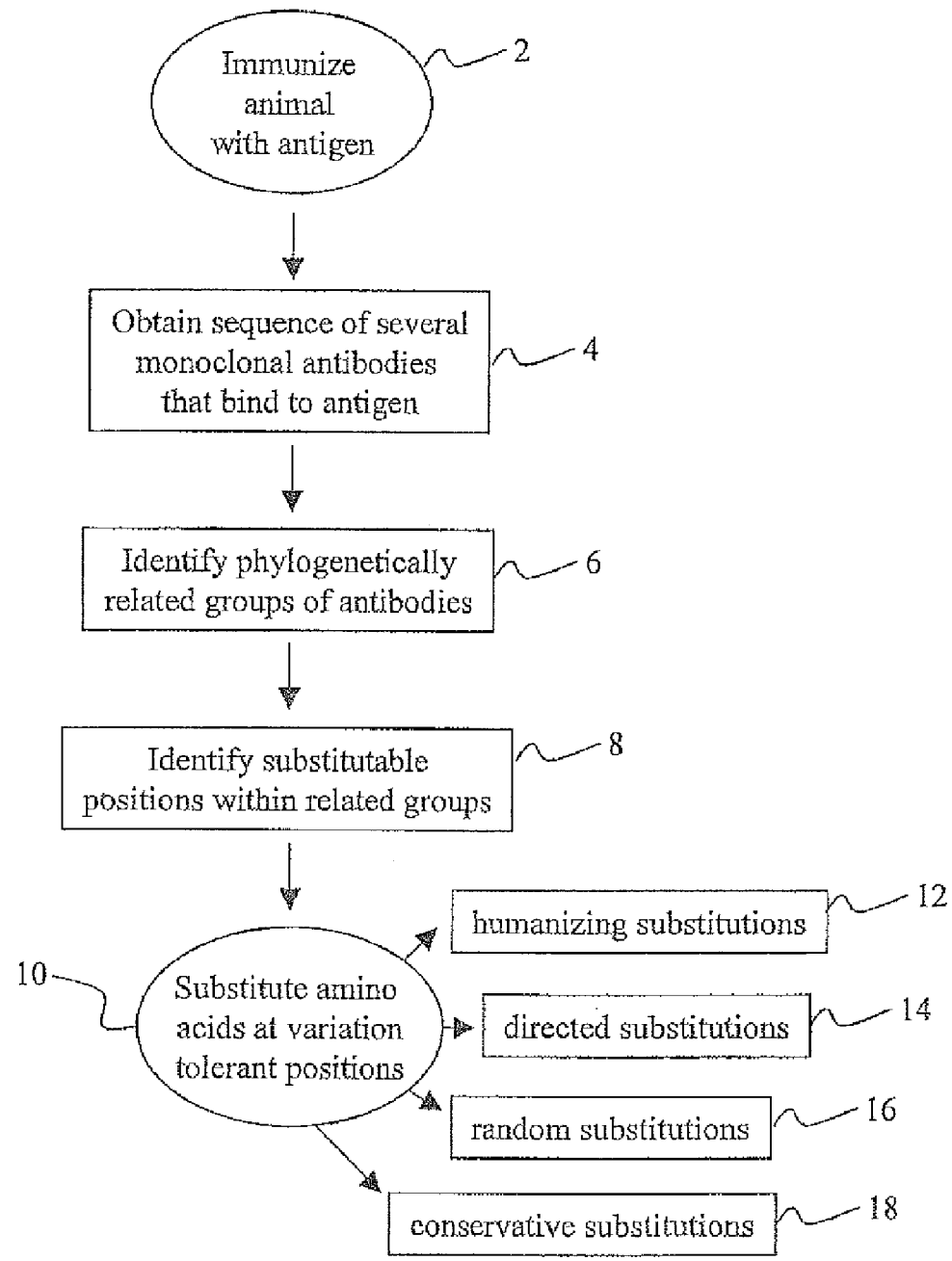
FIG. 1 is a flow diagram illustrating one embodiment of the invention.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific toms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents' thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus: Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to an non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10.000-fold).

In certain embodiments, the affinity between a capture agent and analyte when they are specifically bound in a capture agent/analyte complex is characterized by a $K_D$ (dissociation constant) of less than $10^{-6}$M, less than $10^{-7}$M, less than $10^{-8}$ M, less than le M, less than $10^{-9}$M, less than $10^{-11}$ M, or less than about $10^{-12}$ M or less.

An amino acid residue that is in "close contact", "close proximity" or "in close proximity to" another amino acid residue is an amino acid residue that is has a side chain that is close to, i.e., within 7, 6, 5 or 4 Angstroms, of a side chain of another amino acid. For example, an amino acid that are proximal to a CDR is a non-CDR amino acid that has a side chain that is close to a side chain of an amino acid in a CDR.

A "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Chothia and others (Chothia Structural determinants in the sequences of immunoglobulin variable domain. J Mol Biol 1998; 278:457-79).

VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype and VL is the variable lambda light chain.

A "buried residue" is an amino acid residue whose side chain has less than 50% relative solvent accessibility, which is calculated as the percentage of the solvent accessibility relative to that of the same residue, X, placed in an extended GGXGG peptide. Methods for calculating solvent accessibility are well known in the art (Connolly 1983 J. appl. Crystallogr, 16, 548-558).

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

"Corresponding amino acids", as will be described in greater detail below, are amino acid residues that are at an identical position (i.e., they lie across from each other) when two or more amino acid sequences are aligned. Methods for aligning and numbering antibody sequences are set forth in great detail in Chothia, supra, Kabat supra, and others. As is known in the art (see, e.g. Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected by the immune system of a multi-cellular organism, as opposed to unnaturally paired antibodies made by e.g. phage display. As such, the subject parental antibodies do not usually contain any viral (e.g., bacteriophage M13)-derived sequences. Spleen, lymph nodes and bone marrow are examples of tissues that produce natural antibodies.

A "substitutable position", as will be described in greater detail below, is a particular position of an antibody that may be substituted by different amino acids without significantly decreasing the binding activity of the antibody. Methods for identifying substitutable positions, and how they may be substituted, are described in much greater detail below. A substitutable positions may also be referred to as "variation tolerant position".

A "parent" antibody, as will be described in greater detail below, is an antibody is the target of amino acid substitutions. In certain embodiments, amino acids may be "donated" by a "donor" antibody to the parent antibody to produce an altered antibody.

"Related antibodies", as will be described in greater detail below, are antibodies that have a similar sequence and produced by cells that have a common B cell ancestor. Such a B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies bind to the same epitope of an antigen and are typically very similar in sequence, particularly in their L3 and H3 CDRs. Both the H3 and L3 CDRs of related antibodies have an identical length and a near identical sequence (i.e., differ by 0, 1 or 2 residues), Related antibodies are related via a common antibody ancestor, the antibody produced in the naïve B cell ancestor. The term "related antibodies" is not intended to describe a group of antibodies that do not have a common antibody ancestor produced by a B-cell.

DETAILED DESCRIPTION OF PREFERRED EMBODIMENTS

The invention provides a method for identifying positions of an antibody that can be modified without significantly reducing the binding activity of the antibody. In many embodiments, the method involves identifying a substitutable position in a parent antibody by comparing its amino acid sequence to the amino acid sequences of a number of related antibodies that each bind to the same antigen and epitope as the parent antibody. The amino acid at the substitutable position may be substituted for a different amino acid without significantly affecting the activity of the antibody. The subject methods may be employed to change the amino acid sequence of a CDR without significantly reducing the affinity of the antibody of the antibody, in humanization methods, or in other antibody engineering methods. The invention finds use in a variety of therapeutic, diagnostic and research applications.

In further describing the subject invention, methods of identifying variation-tolerant positions are discussed first, followed by a description of various protocols in which those methods find use.

Methods for Identifying a Variation-Tolerant Position of an Antibody

As mentioned above, the invention provides a method for identifying a variation-tolerant, i.e., substitutable, position of an antibody. Once such a position is identified, the amino acid at that position may be substituted for a different amino acid without significantly decreasing the binding activity of the antibody. The subject method is particularly employable in methods in which it is desirable to identify substitutable residues in regions of an antibody that would otherwise be thought of being essential for antigen binding. For example, the subject methods may be employed to identify substitutable positions in a CDR region of an antibody. In particular embodiments, the subject methods may be employed to identify a substitutable position in a CDR region of an antibody that is to be humanized. Once identified, the amino acid at that position can be substituted for a "human" amino acid (e.g., an amino acid that occupy the equivalent position of a human germline antibody that has a sequence similar the antibody to be humanized). Accordingly, the subject method find particular use in humanization methods, although, as will be described in greater detail below, the subject methods may be readily employed in a wide variety of antibody engineering methods.

In very general terms and with reference to FIG. 1, the subject methods involve immunizing an antibody-producing animal with an antigen 2, and obtaining the amino acid sequence of several monoclonal antibodies that bind to that antigen 4. The amino acid sequences of these antibodies are then compared (e.g., by aligning those sequences), and the antibodies are classified according to their similarity to each other to identify related groups of antibodies 6. The antibodies within each group of related antibodies generally share a common ancestor antibody, and have evolved from that ancestor antibody via somatic hypermutation, gene conversion and other cellular mutation-producing mechanisms that occur during affinity maturation and the final stages of B-cell development. Once groups of related antibodies have been established, the amino acid sequences of the antibodies within a group can be compared to identify substitutable positions 8. A substitutable position of an individual antibody may be identified by virtue of the fact that the identity of the amino acid at that position varies between the individual antibodies of a group of related antibodies. Once identified, the amino acid at the substitutable position of an individual antibody can be substituted for a different amino acid without significantly decreasing the affinity of the antibody 10. Since antibodies containing amino acid substitutions at these substitutable positions were originally produced and effectively tested by the immune system of the initial immunized animal, substitution at those positions should be well tolerated by the antibody. In particular embodiments, an amino acid substitution may be a humanizing substitutions (i.e., a substitution that make the amino acid sequence more similar to that of a human antibody) 12, a directed substitution (e.g., a substitution that make the amino acid sequence of an antibody more similar to that of a related antibody) 14, a random substitution (e.g., a substitution with any of the naturally-occurring amino acids) or a conservative substitution (e.g., a substitution with an amino acid having biochemical properties similar to that being substituted).

As mentioned above, the subject method involves immunizing a suitable animal with an antigen, and obtaining the amino acid sequences of several antigen-reactive antibodies from that animal. The antibody amino acid sequences are usually obtained by sequencing cDNAs encoding the heavy and light chains of those antibodies. The cDNAs are obtained from antibody-producing cells of the animal.

Any suitable animal, e.g., a warm-blooded animal, in particular a mammal such as a rabbit, mouse, rat, camel, sheep, cow or pig or a bird such as a chicken or turkey, may be immunized with a selected antigen using any of the techniques well known in the art suitable for generating an immune response. Procedures for immunizing animals are well known in the art, and are described in Harlow (*Antibodies: A Laboratory Manual*, First Edition (1988) Cold Spring Harbor, N.Y.) and Weir (Handbook of Experimental Immunology Vol 4, Blackwell Scientific Publishers, Oxford, England, 1986). In particular embodiments, a rabbit having an undefined or defined genotype may be employed.

Within the context of the present invention, the phrase "selected antigen" includes any substance to which an antibody may be made, including, among others, polypeptides (including peptides), carbohydrates, inorganic or organic molecules, transition state analogs that resemble intermediates in an enzymatic process, nucleic acids, cells, including cancer cells, cell extracts, pathogens, including living or attenuated viruses, bacteria and the like. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH). Suitable antigens include extracellularly-exposed fragments of Her2, GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUM, MUC18, NCAM (neural cell adhesion molecule), oncofetal fibronectin, PDGFBR (Beta platelet-derived growth factor receptor), PMSA, renal carcinoma antigen G250, RSV, E-Selectin, TGFbeta1, TGFbeta2, TNFalpha, TRAIL-R1, VAP-1 (vascular adhesion protein 1) or VEGF, or the like.

In many embodiments, a peptide having the amino acid sequence corresponding to a portion of an extracellular domain of one of the above-listed proteins is employed as an antigen.

Once a suitable animal has been immunized and an immune response against the antigen has been established by the animal, antibody producing cells from the animal are screened to identify cells that produce antibodies having a desired activity. In many embodiments, these methods may employ hybridoma technology. In other embodiments, however, the methods may employ flow cytometry (FACS) of cell populations obtained from rabbit spleen, bone marrow, lymph node, plasma or other lymph organs, e.g., through incubating the cells with labeled anti-rabbit IgG and sorting the labeled cells using a FACSVantage SE cell sorter (Becton-Dickinson, San Jose, Calif.).

In many embodiments nucleic acids encoding the VH and VL domains of an antibody are isolated from an antibody-producing hybridoma cell. In order to produce antibody-producing hybridoma lines, an animal is immunized with an antigen and once a specific immune response of the rabbit has been established, cells from the spleen of the immunized animal are fused with a suitable immortal cell (e.g., NIH 3T3, DT-40 or 240E cell, etc.; Spieker-Polet et al, Proc. Natl. Acad. Sci. 92: 9348-9352, 1995) to produce hybridoma cells. Supernatants from these hybridoma cells are screened for antibody secretion by enzyme-linked immunosorbent assay (ELISA) and positive clones secreting monoclonal antibodies specific for the antigen can be selected and expanded according to standard procedures (Harlow et al., Antibodies: A Laboratory Manual, First Edition (1988) Cold spring Harbor, N.Y.; and Spieker-Polet et al., supra). Suitable monoclonal antibodies may be further selected in the basis of binding activity, including its binding specificity, binding affinity, binding avidity, a blocking activity or any other activity that causes an effect (e.g. promoting or inhibiting a cellular phenotype, e.g., cell growth, cell proliferation, cell migration, cell viability (e.g., apoptotis), cell differentiation, cell adherence, cell shape changes (e.g., tubular cell formation), complement dependant cytotoxicity CDC, antibody-dependent cell-mediated cytotoxicity ADCC, receptor activation, gene expression changes, changes in post-translational modification (e.g., phosphorylatoin), changes in protein targeting (e.g., NFκB localization etc.), etc., or inhibition of receptor multimerization (e.g., dimer or trimerization) or receptor-ligand interactions).

Antibody-encoding nucleic acids are isolated from these cells using standard molecular biology techniques such as polymerase chain reaction (PCR) or reverse transcription PCR (RT-PCR) (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.).

In particular embodiments, sequences encoding at least the variable regions of the heavy and light chains are amplified from cDNA using techniques well known in the art, such as Polymerase Chain Reaction (PCR). See MUMS, U.S. Pat. No. 4,683,195; Mullis et al., U.S. Pat. No. 4,683,195; Polymerase Chain Reaction: Current Communication in Molecular Biology, Cold Springs Harbor Press, Cold Spring Harbor, N.Y., 1989. Briefly, cDNA segments encoding the variable domain of the antibody are exponentially amplified by performing sequential reactions with a DNA polymerase. The reaction is primed by a 5' and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the immunoglobulin chain. This combination of oligonucleotide primers has been used in the PCR amplification of murine immunoglobulin cDNAs of unknown sequence (see Sastry et al., Proc Natl. Acad. Sci. 86:5728-5732, 1989 and Orlandi et al., Proc. Natl. Acad. Sci. 86:3833-3837, 1989). Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase.

The product is then amplified by PCR using the specific 3' DNA primer and another oligonucleotide consisting of a poly (dC) tail attached to a sequence with convenient restriction sites. In many embodiments, however, the entire polynucleotide encoding a heavy or light chain is amplified using primers spanning the start codons and stop codons of both of the immunoglobulin cDNAs, however, depending on the amplification products desired, suitable primers may be used. In a representative embodiment, rabbit antibody-encoding nucleic acids can be amplified using the following primers: heavy chain, 5' end (CACCATGGAGACTGGGCT-GCGCTGGCTTCTCCTGGTCGCTGTG; SEQ ID NO:49); heavy chain, 3' end (CTCCCGCTCTCCGGGTAAAT-GAGCGCTGTGCCGGCGA; SEQ ID NO:50); light chain kappa, 5'end. (CAGGCAGGACCCAGCATGGACAC-GAGGGCCCCCACT; SEQ ID NO:51); and L kappa, 3'end (TCAATAGGGGTGACTGTTAGAGCGAGACGCCTGC; SEQ ID NO:52). Suitable restriction sites, and other tails may be engineered into the amplification oligonucleotides to facilitate cloning and further processing of the amplification products, Amplification procedures using nested primers may also be used, where such nested primers are well known to one of skill in the art. The variable domains of the antibodies may be sequenced directly from PCR products, or from cloned DNA fragments.

Accordingly an animal is immunized with an antigen, and the amino acid sequence of a plurality (e.g., 2 or more, 3 or more, 5 or more, 10 or more, 15 or more, 20 or more, 30 or more, 50 or more, 80 or more 100 or more, usually up to 500 or 1000 or more) of monoclonal antibodies that bind to that antigen are obtained. In certain embodiments, the monoclonal antibodies are obtained from the cells of a single animal immunized with the antigen.

Figure 4:
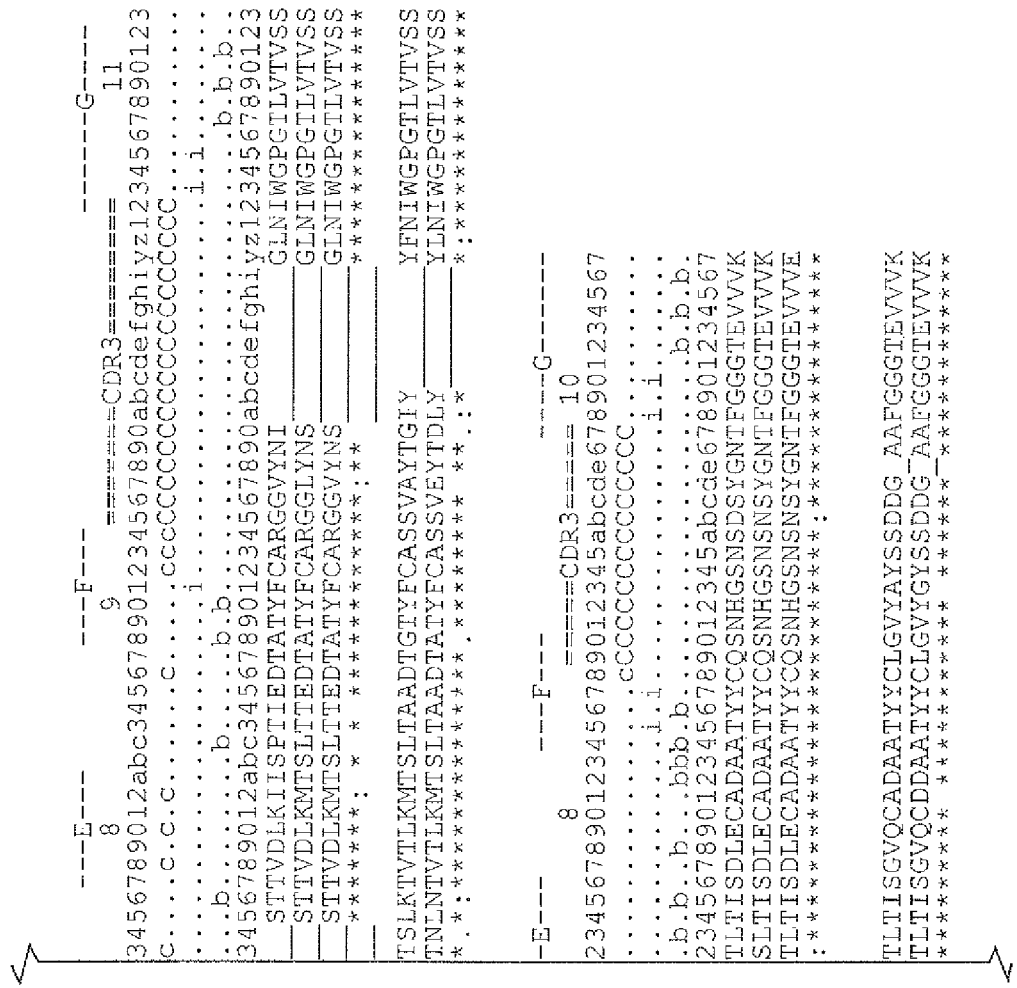
FIG. 4 is an exemplary amino acid sequence alignment. From top to bottom, the amino acid sequences shown in FIG. 4 are SEQ ID NOS: 16-25, Beta strand positions are shown at the top. The adopted numbering system (see Chothia, below) is shown near the top. The following positions are indicated: c: are CDR contacts; i: are at the interface of VK/VH; b: are internal buried residues (see Padlan, below) and C are CDR residues. The sequences are labeled according to convention.

Once the amino acid sequences of the $V_H$ and $V_L$ domains of a set of antigen-binding antibodies have been determined, the amino acids are compared to identify a group of related antibodies that have a similar sequence. This may be done by numbering the amino acid positions of each antibody using a suitable numbering system, such as that provided by Chothia or Kabat supra. CDR and/or framework residues may be identified using these methods. The numbered sequences may be aligned by eye, or by employing an alignment program such as one of the CLUSTAL suite of programs (Thompson et al Nucleic Acids Research, 22:4673-4680). The variable regions of antibodies within a related group of antibodies have amino acid sequences that are very similar. For example, the VH or VL domains of antibodies within a related group of antibodies may have amino acid sequences that are at least about 90% identical (e.g., at least 95% or at least 98% or at least 99% identical), ignoring any gaps or insertions made to facilitate alignment of the sequences. Antibodies within a related group of antibodies have a VL domains that are similar to each other, as well as VH domains that are similar to each other. In other words, in certain embodiments the VH or VL domains of two different related antibodies usually contain up to about five (i.e., one, two, three, four or five or more) amino acid differences. An amino acid difference may be present at any position of the variable domain, including in any CDR or in any framework region. Related rabbit antibodies have 113 CDRs that are almost identical, as well as L3 CDRs that are almost identical. In these embodiments, any two antibodies that are related will have L3 and H3 CDRs that are each identical in length and have near identical sequences (i.e., that contain 0, 1 or 2 amino acid changes). In other words the L3 CDRs of the two antibodies are identical in length and near identical in sequence and the H3 CDRs of the two antibodies are identical in length and near identical in sequence. Two exemplary sets of related antibodies are shown in FIG. 4, and the sequences of 20 exemplary VH3 regions of unrelated rabbit antibodies are shown for comparison.

Depending on the particular antigen used, the species and genotype of the animal used, and the number of antibody-encoding nucleic acids sequenced, a relatively low number (e.g., less than about 5 or 10 groups may be identified). In certain embodiments, only one or two groups may be identified. The antibodies within each group display greater than 90% sequence to each other, whereas any two antibodies of any two different groups typically display less than 90% to each other, across the entire length of the variable domains of the antibodies.

In order to identify a substitutable position of an antibody, the amino acid sequence of that antibody is compared to the sequences of other antibodies belonging to the same group as that antibody. If the identity of that amino acid varies between the different related antibodies of a group at any particular position, that position is a substitutable position of the antibody. In other words, a substitutable position is a position in which the identity of the amino acid varies between the related antibodies. Positions that contain a constant amino acid are not substitutable positions.

This aspect of the invention may be exemplified with reference to FIG. 2. FIG. 2 shows an exemplary amino acid sequence alignment of 10 different exemplary, hypothetical, antibodies that are related. The amino acid sequences of the framework regions (FW) of these antibodies are omitted from FIG. 2, although the principles discussed above and below are readily applicable to framework sequences. At each position the amino acid can be invariable (i.e., constant) or variable (may change) from on antibody to another. In the example shown in FIG. 2, the amino acid at positions a, b, d, a, g, h, r, j, k, m, n, o, q, r, s, u, v, w, x, z and a are constant, whereas the amino acids at positions c, f, l, p, t and y are variable. Positions c, f, l, p, t and y are substitutable (or variation tolerant) positions whereas positions a, b, d, e, g, h, i, j, k, m, n, o, q, r, s, u, v, w, x, z and a are not substitutable positions.

Figure 7:
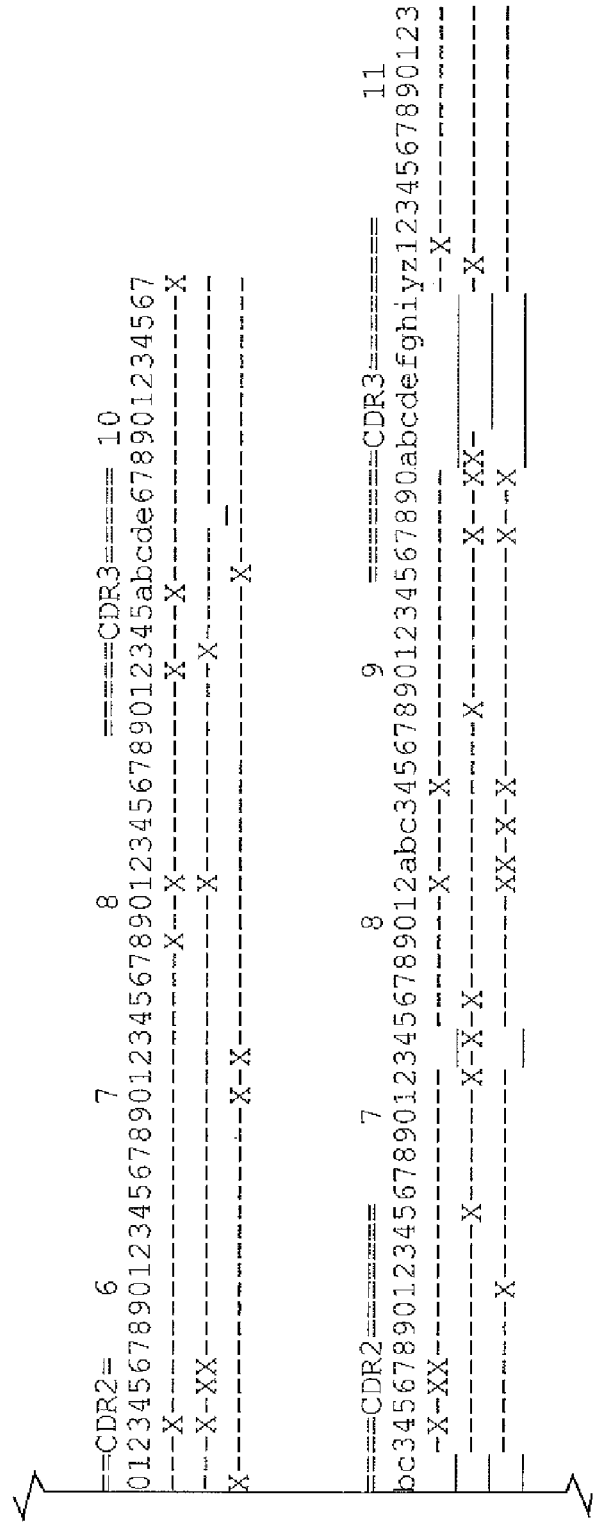
FIG. 7 shows an exemplary amino acid sequence alignment illustrating how a consensus sequence for an antibody can be made.

In a further embodiment, the above method may be employed to provide a consensus antibody sequence. In such a consensus sequence, a non-substitutable position is indicated by the amino acid present at that position, and a substitutable position is indicated as an "X". Depending on how the antibodies are to be employed, X may be a) any amino acid, b) any amino acid present at that position in any of the related antibodies in the group or a conservatively substituted variant thereof or c) any amino acid present at that position in any of the related antibodies in the group. For example, in the example shown in FIG. 2, the antibody consensus has a sequence: RTXATXCLFQ-FW1-RXWTVXA-FW2-PSX-SHTVXIT (SEQ ID NO:54), where X can be any amino acid, any amino acid present at that position in a related antibody, or a conservatively substituted amino acid present at that position in a related antibody. Any antibody having a sequence that is encompassed by the consensus should bind to the same antigen as any of the related antibodies. Exemplary consensus sequences for the heavy and light chains of three sets of related antibodies that bind to TNFα are shown in FIG. 7. The non-X amino acids are the same as those shown at the equivalent position of the antibody sequences shown in FIG. 4. In certain embodiments, a consensus sequence may only contain the amino acid sequence of the CDR regions of an antibody.

Substituting an Amino Acid at a Substitutable Position

The method described above may be employed in methods of designing and making a variant of a parental antibody that at least maintains (i.e. maintains or increases) the antigen binding activity of the parental antibody. Because antibodies containing substitutions at substitutable positions have already been produced and tested by an immunized animal, substitutions at those positions can be made in the knowledge that they should not significantly decrease the binding activity of the antibody. In general, an antibody variant of a parental antibody has an antigen binding affinity that is at least 10%, at least 20%, at least 30%, at least 40%, at least 50%, at least 60%, at least 70%, at least 80%, at least 90% or at least 100% (e.g., at least 150%, at least 200%, at least 500%, at least 1000%, usually up to at least 10,000%) of the binding affinity of the parental antibody to a particular antigen.

As illustrated in FIG. 1, a substitutable position of a parental antibody may be substituted by a) any of the 20 naturally occurring amino acids to produce random substitutions, b) an amino acid having biochemical properties similar to the amino acid already present at the substitutable position to produce conservative substitutions, c) an amino acid that is present at the same position in a related antibody to produce a directed substitution, or d) an amino acid that is present at the same position in a similar human antibody to produce a humanizing substitution. A substitution may be made at any part of an antibody variable region, including any framework region or CDR In certain embodiments, a single substitutable amino acid may be substituted. However, in other embodiments, a plurality of substitutable amino acids (e.g., up to about 5 or 10 ore more) may be substituted. In particular embodiments, the type of substitution that can be made at each substitutable position may be indicated by the types of amino acids present at that position in the related antibodies. For example, if unrelated amino acids (e.g., ala, gly, cys, glu and thr) are present at a certain position of a group of related antibodies, then any amino acid could be substituted at that position without significantly reducing binding activity of the antibody. Similarly, if a subset of nonpolar amino acids (e.g., val, ile, ala and met) are present at a certain position of a set of related antibodies, then other non-polar amino acids (e.g., leu) could be substituted at that position without significantly reducing binding activity of the antibody.

In any of these methods, the resultant antibody variants may be tested to confirm that any binding activities have not been significantly reduced by substitution. Further, and as will be described in greater detail below, a library of variant antibodies that contain a plurality of substituted amino acids may be produced, and screened to provide an antibody with an improved activity. For example, one or more substitutable positions of an antibody may be substituted by any combination of random, conservative or directed substitutions to produce a library of variants that are each individually tested to identify an antibody having an improved binding activity.

Conservative Substitutions

The amino acid at a substitutable position of an antibody may be replaced by an amino acid having similar properties (based on size, polarity, hydrophobicity, and the like) to the amino acid to be replaced. In other words, the amino acid at a substitutable position of an antibody can be replaced with a different amino acid of the same class, where the amino acids may be classified as follows: aromatic: phe, tyr, trp; apolar: leu, val, ile, ala, met; aliphatic: ala, val, leu, ile; acidic: asp, glu; basic: his, lys, arg; polar: gln, asn, ser, thr, tyr. In certain embodiments, the amino acid at a substitutable position of an antibody may be replaced according to the following table:

| amino acid to be replaced | replacing amino acid |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Directed Substitutions

The amino acid at a substitutable position of an antibody may be replaced by a different amino acid that is present at the same position in a related antibody (i.e., a related antibody). For example and with reference to FIG. 2, the ala at substitutable position c in antibody I could be replaced with a gly, cys, glu or a thr since these amino acids are found at substitutable position c in antibodies 3, 5, 7 and 10, respectively; the met at substitutable position f in antibody I could be replaced with a val or an ile, since these amino acids are found at substitutable position f in antibodies 4 and 8, respectively; the phe at substitutable position 1 in antibody 1 could be replaced with a tyr or trp, since these amino acids are found at substitutable position l in antibodies 6 and 9, respectively, and so on for positions p, t and y of antibody 1.

Humanizing Substitutions

The amino acid at a substitutable position of a parental antibody may be replaced by a different amino acid that is present at the same position of a human antibody. In these embodiments, the amino acid sequence of the variable domain of a parental antibody is usually compared to a database of human antibody sequences, and a human antibody that has an amino acid sequence that is similar to that of the parental antibody is selected. The amino acid sequence of the parental antibody and the human antibody are compared (e.g., aligned), and one or more substitutable amino acids of the parental antibody are substituted by correspondingly positioned amino acids in the human antibody. This embodiment is exemplified in the top panel of FIG. 3, where all substitutable amino acids are substituted for their human counterpart. The bold underlined amino acids of the humanized sequence (hmAb) indicate amino acids that have been substituted. The bold double-underlined amino acids have not been substituted since the "human" amino acid was already present in the parental antibody.

In a refinement of this embodiment, the humanizing substitution may be a directed substitution in which an amino acid at a substitutable position is substituted for an amino acid that is present in both the human antibody and a related antibody. This embodiment is illustrated in the bottom panel of FIG. 3. In this figure, the ala at position c of antibody 1 is substituted with a thr, where a thr is found at that position in both antibody 10 (as shown in FIG. 2) and a similar human antibody. Further, the gin at position y of antibody I is substituted with a tyr, where a tyr is found at that position in both antibody 9 (as shown in FIG. 2) and a similar human antibody. Other substitutable amino acids (i.e., those at positions f, l, p and t) are not substituted in this embodiment since none of the related antibodies have the same amino acid as the human antibody at this position.

In other embodiments, the substituting amino acids may be chosen as being less polar than the other amino acids, and therefore less immunogenic.

A suitable human antibody for use in these methods is identified by comparing the heavy and light chain variable domain sequences of the parental antibody (or a consensus sequence of set of related antibodies) to a database of human antibody sequences. Typically, one of the 10 most similar sequences in terms of amino acid sequence identity (either by percent identity or P-value) will be employed as an amino acid residue donor. In certain embodiment, one of the three most similar antibodies (e.g., the most similar) in terms of amino acid sequence identity (percent identity or P-value) to a parental antibody sequence may be used as an amino acid residue donor. The selected human antibody and the parental antibody will typically have at least about 55%, at least about 65% identity, at least about 75%, at least about 80%, at least about 85%, at least about 90%, or at least about 95% amino acid sequence identity across the entire variable domain in one or both of the sequenced chains. In certain embodiments, both the light and heavy chains from the same human antibody may be used as amino acid donors. In most embodiments, the parental antibody is compared to human germ-line antibody sequences.

Various antibody databases can be searched to identify the most homologous human antibody immunoglobulins for a given rabbit immunoglobulin sequence. In addition to National Center for Biotechnology Information (NCBI) databases, several of the most commonly used databases are listed below:

V BASE—Database of Human Antibody Genes: This database is maintained by the medical research council (MRC), of Cambridge UK and is provided via the website: www.mrc-cpe.cam.ac.uk. This database is comprehensive directory of all human germline variable region sequences compiled from over a thousand published sequences, including those in the current releases of the Genbank and EMBL data libraries.

Kabat Database of Sequences of Proteins of Immunological Interest (Johnson, G and Wu, TT (2001) Kabat Database and its applications: future directions. Nucleic Acids Research, 29: 205-206) found at the website of Northwestern University, Chicago (immuno.bme.nwu.edu).

Immunogenetics Database: Maintained by and found at the website of the European Bioinformatics Institute: www.ebi.ac.uk. This database is integrated specialized database containing nucleotide sequence information of genes important in the function of the immune system. It collects and annotates sequences belonging to the immunoglobulin superfamily which are involved in immune recognition.

ABG: Germline gene directories of the mouse—a directory of mouse VH and VK germline segments, part of the webpage of the Antibody Group at the Instituto de Biotecnologia., UNAM (National Univfrsity of Mexico)

Built-in searching engines can be used to search for most similar sequences in terms of amino acid sequence homology. In the methods of this invention, BLAST (Altschul at al., J. Mol. Biol. 215:40340, 1990) is performed using default parameters, including choosing the BLOSUM62 matrix, an expect threshold of 10, low complexity filter off, gaps allowed, and a word size of 3.

During the subject humanization methods, one, two, three, four, five or six or more, usually up to about 10 or more, humanizing amino acid substitutions are made, Non-consecutive amino acids are generally substituted in these methods.

The above-described methods for making humanizing substitutions in an antibody may be employed as an alternative to, in combination with, or in addition to known antibody humanization methods such as the CDR grafting and resurfacing methods discussed in the introduction.

For example, the subject humanization methods may be incorporated into any humanization method that requires making amino acid substitutions in a parental antibody to make it more similar to a known human antibody (see, e.g., U.S. patent application Ser. Nos. 10/638,210 and 10/637,317, both filed on Aug. 7, 2003, and other references cited in the background, all incorporated by reference herein in their entirety). For example, many prior humanization methods are directed to identifying particular amino acids in a parental antibody that can be substituted by a human amino acid (i.e., the amino acid found at the same position in a human antibody). As a refinement of these prior methods, the instant methods can be employed to identify which of those particular amino acids are substitutable amino acids and are therefore variation tolerant. Since amino acid substitutions at these substitutable positions are readily tolerated by an antibody (i.e., they don't significantly decrease binding affinity), humanizing amino acid substitutions can be made without significantly reducing antibody activity. For example, only substitutable positions that are on the surface of an antibody and not in a significant area of secondary structure may be substituted by a human amino acid. In addition, the method may be employed in combination with methods for removing helper T cell epitopes from an antibody, such as the "deimmunization" methods described in published U.S. Patent No. 20030153043 and others. For example, only deimmunizing amino acid changes that occur at substitutable positions may be made. Such changes should not abolish antibody activity.

In particular embodiments, the subject methods may be employed to humanize the CDRs of an antibody. These embodiments may be employed in addition to other humanization methods that are directed to humanizing the framework regions and other non-CDR regions of an antibody, for example.

The humanization methods described above represent a significant contribution to the antibody humanization arts because no other humanization method can be employed to substitute only those positions of an antibody that are known to be tolerant to substitutions.

Further, since the instant methods effectively employ the amino acid sequences of variant antibodies that have been selected as having strong binding activity by the immune system of the immunized animal (by affinity maturation), substituting an amino acid at a substitutable position of an antibody identified by the above methods often leads to an increase in binding affinity. This is particularly true of antibodies that have been subjected to directed substitutions, as described above. Accordingly, in general, the instant humanization methods may be employed to humanize a parental antibody to produce a humanized antibody that has a greater binding affinity for an antigen than the parental antibody.

Methods of Improving Antibody Activity

In one embodiment of particular interest, the instant substitutions methods may be employed to improve a binding activity of a parental antibody. As noted above, the substitutable positions identified by the subject methods are sites that are employed to improve the binding activity of a progenitor antibody during affinity maturation. Those positions, and the amino acids present into those positions in the group of related antibodies, were selected as increasing the affinity of an antibody to a particular antigen. By combining the individual changes made to an antibody during affinity maturation, an antibody having an increased affinity for an antigen may be produced. In certain embodiments, therefore, a plurality of directed substitutions may be made in a parental antibody to increase the affinity of that antibody. For example, a parental antibody may be modified to contain the most common substitution at each of the substitutable positions of a group of related antibodies.

In a related method, if a sufficient number of antibodies (e.g., more then 20 and up to about 50 or more) are sequenced, particular antibody activities (e.g., antibody binding affinity, antibody binding avidity, antibody binding specificity, etc.) of those antibodies can be correlated with particular amino acid changes. This knowledge allows an antibody having a combination of selected binding activities to be designed and made.

Further, and as mentioned above, the identification of substitutable positions of an antibody facilitates the production of libraries of candidate antibodies to be screened to identify an antibody have a desired binding activity. In one example, this method involves making every possible combination of amino acid substitutions (e.g., any combination of directed, random and/or conservative substitutions for example) at substitutable positions of an antibody to produce an antibody library that can be screened to identify an antibody having an improved properties.

Suitable methods for screening antibodies are well known in the art, and include but are not limited to the following:

Binding Assays

In these assays, each antibody of a subject library is tested for its ability to bind specifically to a substrate. The term "specifically" in the context of antibody binding, refers to high avidity and/or high affinity binding of an antibody to a specific antigen i.e., a polypeptide, or epitope. In many, embodiments, the specific antigen is an antigen (or a fragment or subfraction of an antigen) used to immunize the animal host from which the antibody-producing cells were isolated. Antibody specifically binding an antigen is stronger than binding of the same antibody to other antigens. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a KD of $10^{-7}$ M or less, e.g., $10^{-8}$ M or less (e.g., $10^{-9}$ M or less, $10^{40}$ or less, $10^{-11}$ or less $10^{-12}$ or less, or $10^{513}$ less, etc.). In general, an antibody with a binding affinity KD of $10^{-7}$ M or greater is not useful in that it will not bind an antigen at a detectable level using conventional methodology currently used.

Typically, in performing a screening assay, antibody samples produced by a library of antibody producing host cells are deposited onto a solid support in a way that each antibody can be identified, e.g. with a plate number and position on the plate, or another identifier that will allow the identification of the host cell, culture that produced the antibody.

The antibodies of the invention may be screened for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine mid well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally involve lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally involves preparation of protein samples followed by electrophoresis of the protein samples in a polyacrylamide gel (e.g., 8%-20% SDS-PAGE depending on the molecular weight of the antigen), and transfer of the separated protein samples from the polyacrylamide gel to a membrane such as nitrocellulose, PVDF or nylon. Following transfer, the membrane is blocked in blocking solution (e.g., PBS with 3% BSA or non-fat milk), washed in washing buffer (e.g., PBS-Tween 20), and incubated with primary antibody (the antibody of interest) diluted in blocking buffer. After this incubation, the membrane is washed in washing buffer, incubated with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I), and after a further wash, the presence of the antigen may be detected. One of skill in the art would be knowledgeable as to the parameters that can be modified to increase the signal detected and to reduce the background noise.

ELISAs involve preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmuno assays. In this case, the antigen is incubated with antibody of interest conjugated to a labeled compound (e.g., 3H or 125I) in the presence of increasing amounts of an unlabeled second antibody.

Antibodies of the invention may be screened using immunocytochemistry methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

In certain embodiments, however, the assay is an antigen capture assay, and an array or microarray of antibodies may be employed for this purpose. Methods for making and using microarrays of polypeptides are known in the art (see e.g. U.S. Pat. Nos. 6,372,483, 6,352,842, 6,346,416 and 6,242,266).

Inhibitor Assays

In certain embodiments, the assay measures the specific inhibition of an antibody to an interaction between a first compound and a second compound (e.g. two biopolymeric compounds) or specifically inhibits a reaction (e.g. an enzymatic reaction). In the interaction inhibition assay, one interaction substrate, usually a biopolymeric compound such as a protein e.g. a receptor, may be bound to a solid support in a reaction vessel. Antibody is added to the reaction vessel followed by a detectable binding partner for the substrate, usually a biopolymeric compound such as a protein e.g. a radio-labeled ligand for the receptor. After washing the vessel, interaction inhibition may be measured by determining the amount of detectable binding partner present in the vessel. Interaction inhibition occurs when binding of the binding partner is reduced greater than about 20%, greater than about 50%, greater than about 70%, greater than about 80%, or greater than about 90% or 95% or more, as compared to a control assay that does not contain antibody.

In the reaction inhibition assay, an enzyme may be bound to a solid support in a reaction vessel. Antibody is usually added to the reaction vessel followed by a substrate for the enzyme. In many embodiments, the products of the reaction between the enzyme and the substrate are detectable, and, after a certain time, the reaction is usually stopped. After the reaction has been stopped, reaction inhibition may be measured by determining the level of detectable reaction product present in the vessel. Reaction inhibition occurs when the rate of the reaction is reduced greater than about 20%, greater than about 50%, greater than about 70%, greater than about 80%, or greater than about 90% or 95% or more, as compared to a control assay that does not contain antibody.

In Vivo Assays

In certain embodiments the antibodies are tested in vivo. In general, the method involves administering a subject monoclonal antibody to an animal model for a disease or condition and determining the effect of the monoclonal antibody on the on the disease or condition of the model animal. In vivo assays of the invention include controls, where suitable controls include a sample in the absence of the monoclonal antibody. Generally a plurality of assay mixtures is run in parallel with different antibody concentrations to obtain a differential response to the various concentrations. Typically, one of these concentrations serves as a negative control, i.e. at zero concentration or below the level of detection.

Substituted Antibodies

The present invention provides substituted antibodies that are substituted by the method set forth above.

In general, a substituted antibody retains specificity for an antigen as compared to a parent antibody, has substantial affinity (e.g. at least $10^7 M^{-1}$, at least $10^8 M^{-1}$, or at least $10^9 M^{-1}$ to $10^{10} M^{-1}$ or more) to that antigen, and, if humanized, is usually less immunogenic in a human host, as compared to a parent antibody.

The level of immunogenicity of a humanized antibody as compared to a parent rabbit antibody in a human host may be determined by any of a number of means, including administering to a single human host a formulation containing equimolar amounts of the two isolated antibodies and measuring the immune response of the human host relative to each of the antibodies. Alternatively, the parent and modified antibodies are administered separately to different human hosts and the immune response of the hosts are measured. One suitable method for measuring the immune response of the host relative to each of the antibodies is by ELISA (described in Ausubel, et al, *Short Protocols in Molecular Biology*, 3rd ed., Wiley & Sons, 1995, UNIT 11-4), where a suitable equal amount of each antibody is spotted into the wells of a microtitre plate, and the assay is performed polyclonal antiserum from the human host. In most embodiments, a subject humanized antibody is about 10% less immunogenic, about 20% less immunogenic, about 30% less immunogenic, about 40% less immunogenic, about 50% less immunogenic, about 60% less immunogenic, about 80% less immunogenic, about 90% less immunogenic or even about 95% less immunogenic than an unmodified parent antibody.

Depending on the constant regions and other regions used, several types of antibody that are known in the art may be made. As well as full length antibodies, antigen-binding fragments of antibodies may be made by the subject methods. These fragments include, but are not limited to, Fab, Fab' and $F(ab)_2$, Fd, single-chain Fvs (scFv), single-chain immunoglobulins (e.g., wherein a heavy chain, or portion thereof, and light chain, or portion thereof, are fused), disulfide-linked Fvs (sdFv), diabodies, triabodies, tetrabodies, scFv minibodies, Fab minibodies, and dimeric scFv and any other fragments comprising a $V_L$ and a $V_H$ domain in a conformation such that a specific antigen binding region is fowled. Antibody fragments, including single-chain antibodies, may comprise the variable region(s) alone or in combination with the entire or partial of the following: a heavy chain constant domain, or portion thereof, e.g., a CH1, CH2, CH3, transmembrane, and/or cytoplasmic domain, on the heavy chain, and a light chain constant domain, e.g., a $C_{Kappa}$ or $C_{lambda}$ domain, or portion thereof on the light chain. Also included in the invention are any combinations of variable region(s) and CH1, CH2, CH3, $C_{kappa}$, $C_{lambda}$, transmembrane and cytoplasmic domains. By the term "antibody" is meant any type of antibody, including those listed above, in which the heavy and light chains have been, as explained above, naturally paired, i.e., excluding so-called "phage-display" antibodies.

Nucleic Acids Encoding Substituted Antibodies

The invention further provides nucleic acids comprising a nucleotide sequence encoding a subject modified antibody, as well as portions thereof, including a light or heavy chain, a light or heavy chain variable domain, or a framework region of a light or heavy chain variable domain. Subject nucleic acids are produced by a subject method. In many embodiments, the nucleic acid also comprises a coding sequence for a constant domain, such as a constant domain of any human antibody. Nucleic acids encoding a human immunoglobulin leader peptide (e.g. MEFGLSWVFLVAILKGVQC, SEQ ID NO:53) may be engineered to allow the secretion of the antibody chains.

Since the genetic code and recombinant techniques for manipulating nucleic acid are known, and the amino acid sequences of the subject antibodies may be obtained using the method described above, the design and production of nucleic acids encoding a substituted antibody is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, antibody coding sequences may be isolated from antibody-producing cells using any one or a combination of a variety of recombinant methods that do not need to be described herein. Subsequent substitution, deletion, and/or addition of nucleotides in the nucleic acid sequence encoding a protein may also be done use standard recombinant DNA techniques.

For example, site directed mutagenesis and subcloning may be used to introduce/delete/substitute nucleic acid residues in a polynucleotide encoding an antibody. In other embodiments, PCR may be used. Nucleic acids encoding a polypeptide of interest may also be made by chemical synthesis entirely from oligonucleotides (e.g., Cello et al., Science (2002) 297:1016-8).

In certain embodiments, the codons of the nucleic acids encoding polypeptides of interest are optimized for expression in cells of a particular species, particularly a mammalian, e.g., human, species.

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell. One suitable vector is pCMV, which used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The subject nucleic acids usually comprise an single open reading frame encoding a subject antibody, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic, or any other, host cell, including viral promoters and promoters derived from eukaryotic or prokaryotic genes. Exemplary eukaryotic promoters include, but are not limited to, the following: the promoter of the mouse metallothionein I gene sequence (Hamer et al., I. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

The subject nucleic acids may also contain restriction sites, multiple cloning sites, primer binding sites, ligatable ends, recombination sites etc., usually in order to facilitate the construction of a nucleic acid encoding a humanized rabbit antibody.

In general, several methods are known in the art for producing antibody-encoding nucleic acids, including those found in U.S. Pat. Nos. 6,180,370, 5,693,762, 4,816,397, 5,693,761 and 5,530,101. One PCR method utilizes "overlapping extension PCR" (Hayashi et al., Biotechniques. 1994: 312, 314-5) to create expression cassettes for the heavy and light chain encoding nucleic acids. In this method multiple overlapping PCR reactions using the cDNA product obtained from the antibody producing cell and other appropriate nucleic acids as templates generates an expression cassette.

Methods for Producing Antibodies

In many embodiments, the nucleic acids encoding a subject monoclonal antibody are introduced directly into a host cell, and the cell incubated under conditions sufficient to induce expression of the encoded antibody.

Any cell suitable for expression of expression cassettes may be used as a host cell. Far example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al. J. Gen Viral, 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TIM, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MIDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH13T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiment, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Determining Binding Affinity of an Antibody

Once a modified antibody is produced, it may be tested for affinity using any known method, such as: 1) competitive binding analysis using a labeled (radiolabeled or fluorescent labeled) parent antibody, a modified antibody and an antigen recognized by the parent antibody; 2) surface plasmon resonance using e.g. BIACore instrumentation to provide the binding characteristics of an antibody. Using this method antigens are immobilized on solid phase Chips and the binding of antibodies in liquid phase are measured in a real-time manner; and 3) flow cytometry, for example, by using fluorescent activated cell sorting (FACS) analysis to study antibody binding to cell surface antigens; 4) ELISA; 5) equibrilium dialysis, or FACS. In this FACS method both transfected cells and native cells expressing the antigen can be used to study antibody binding. Methods for measuring binding affinity are generally described in Harlow et al., *Antibodies: A Laboratory Manual*, First Edition (1988) Cold spring Harbor, N.Y.; Ausubel, et al, *Short Protocols in Molecular Biology*, 3rd ed., Wiley & Sons, 1995).

If affinity analysis reveals a decrease in antibody binding for the modified antibody as compared to its parent antibody, "fine tuning" may be performed to increase the affinity. One method of doing this is to systematically change back each modified residues by site-directed mutagenesis. By expressing and analyzing these back mutant antibodies, one would predict the key residues that cannot be modified unless without decreasing affinity.

Utility

An antibody produced by the instant methods finds use in diagnostics, in antibody imaging, and in treating diseases treatable by monoclonal antibody-based therapy. In particular, an antibody humanized by the instant methods may be used for passive immunization or the removal of unwanted cells or antigens, such as by complement mediated lysis or antibody mediated cytotoxicity (ADCC), all without substantial immune reactions (e.g., anaphylactic shock) associated with many prior antibodies. For example, the antibodies of the present invention may be used as a treatment for a disease where the surface of an unwanted cell specifically expresses a protein recognized the antibody (e.g. HER2, or any other cancer-specific marker) or the antibodies may be used to neutralize an undesirable toxin, irritant or pathogen. Humanized antibodies are particularly useful for the treatment of many types of cancer, for example colon cancer, lung cancer, breast cancer prostate cancer, etc., where the cancers are associated with expression of a particular cellular marker. Since most, if not all, disease-related cells and pathogens have molecular markers that are potential targets for antibodies, many diseases are potential indications for humanized antibodies. These include autoimmune diseases where a particular type of immune cells attack self-antigens, such as insulin-dependent diabetes mellitus, systemic lupus erythematosus, pernicious anemia, allergy and rheumatoid arthritis; transplantation related immune activation, such as graft rejection and graft-vs-host disease; other immune system diseases such as septic shock; infectious diseases, such as viral infection or bacteria infection; cardiovascular diseases such as thrombosis and neurological diseases such as Alzheimer's disease. An antibody of particular interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are tanned "therapeutic" antibodies.

Kits

Also provided by the subject invention are kits for practicing the subject methods, as described above. The subject kits at least include one or more of: a substituted antibody made according to the above methods, a nucleic acid encoding the same, or a cell containing the same. The substituted antibody may be humanized. Other optional components of the kit include: restriction enzymes, control primers and plasmids; buffers; etc. The nucleic acids of the kit may also have restrictions sites, multiple cloning sites, primer sites, etc to facilitate their ligation to non-rabbit antibody CDR-encoding nucleic acids. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention is are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification of Variation Tolerant Amino Acids in an Anti-TNFα Rabbit Monoclonal Antibody A rabbit was immunized with TNFα, the spleen of that rabbit was used to make hybridoma cells, and hybridoma cells expressing anti-TNFα, monoclonal antibodies were isolated. cDNAs encoding the heavy and light chains of those monoclonal antibodies were isolated from the isolated cells, and sequenced. The polypeptides encoded by the cDNAs were aligned according to their structural features, and this alignment is shown in FIG. 4, FIG. 4 shows that two groups of related anti-TNFα rabbit monoclonal Abs were obtained, Antibodies 52, 63, and 115 belong to one group. Antibodies 1 and 204 belong to a different group. Positions indicated by an asterisk (*) are non-variant positions, wherein positions indicated by a period (.) or colon (:) are variant tolerant positions. Many variation tolerant positions are within the CDRs.

FIG. 2 is a multiple sequence alignment of the H3 region of ten rabbit antibody sequences extracted from the Kabat database to illustrate the expected variation in unrelated antibodies.

Example 2

Humanizing an Anti-TNFα Rabbit Monoclonal Antibody

The sequence of a rabbit anti-TNFα rabbit monoclonal antibody A52 is aligned with the most similar human germline antibody, L20, and variation tolerant positions of the rabbit anti-TNFα rabbit monoclonal antibody are substituted with amino acids at the corresponding positions of the L20 antibody to produce a humanized rabbit antibody (HZD). The substituted amino acids are marked by stars. According to FIG. 4, position 31 (within a CDR) is a variation tolerant position because it is an N or an S. N was chosen since that is found in the human germline antibody at that position. According to FIG. 4, position 48 (just outside a CDR) is a variation tolerant position because it is an M or an I. I was chosen since that is found in the human germline antibody at that position. According to FIG. 4, position 50 (within a CDR), is a variation tolerant position because it is an L or a V. This position was substituted with an A since A is the amino acid found in the human germline antibody at that position. According to FIG. 4, position 70 (within a framework region), is a variation tolerant position because it is an E or a Q. This position was substituted with a D because D is found in the human germline antibody at this position. According to FIG. 4, position 95B (within a CDR) is a variation tolerant position because it is a D or an N. This position was substituted with an N since N is less polar than N and therefore likely to be less immunogenic.

It is evident from the above results and discussion that the subject invention provides an important new means for making amino adds changes to an antibody. As such, the subject methods and systems find use in a variety of different applications, including research, agricultural, therapeutic and other applications. In particular, the invention provides a means for humanizing the antigen binding region (e.g., the CDR regions) of a non-human antibody. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of altering the amino acid sequence of the framework of an antibody, comprising:
    a) identifying a variation tolerant position in a framework sequence of a parent antibody by comparing the amino acid sequence of said parent antibody to the amino acid sequence of a related antibody that is obtained from the same animal as said parent antibody, wherein said parent antibody and said related antibody:
        i. bind to the same antigen;
        ii. have H3 CDRs that are identical in length and identical in sequence except for 0, 1 or 2 amino acid substitutions relative to one another;
        iii. have L3 CDRs that are identical in length and identical in sequence except for 0, 1 or 2 amino acid substitutions relative to one another; and
        iv. have at least one amino acid substitution in a framework sequence relative to one another; and
    b) substituting the amino acid present at said variation tolerant position in said framework with a different amino acid to produce an altered antibody that binds the same antigen as the parent antibody.

2. The method of claim 1, wherein the amino acid of said variation tolerant position of said framework sequence of said parent antibody is substituted by an amino acid present at a corresponding position in said related antibody.

3. The method of claim 1, wherein the amino acid of said variation tolerant position of said framework sequence of said parent antibody is substituted by an amino acid present at a corresponding position in a human antibody.

4. The method of claim 1, wherein said substituting comprises making a conservative amino acid substitution.

5. The method of claim 1, further comprising altering one or more CDRs of said parent antibody.

6. The method of claim 1, wherein said method comprises identifying and substituting at least two variant tolerant positions in the framework of said parent antibody.

7. The method of claim 1, further comprising testing said altered antibody for binding to said antigen.

8. The method of claim 7, wherein said testing is done by ELISA.

9. The method of claim 1, wherein said parent and said related antibodies are rabbit antibodies.

10. The method of claim 1, further comprising:
    introducing a nucleic acid encoding said altered antibody into a cell;
    culturing said cell to produce said altered antibody; and
    isolating said altered antibody from said cell.

11. The method of claim 1, wherein:
    said animal is a rabbit or a mouse; and
    the amino acid of said variation tolerant position of said framework sequence of said parent antibody is substituted in step b) by an amino acid present at a corresponding position in a human antibody.

* * * * *